United States Patent
Sullivan et al.

(10) Patent No.: US 10,492,756 B2
(45) Date of Patent: Dec. 3, 2019

(54) CORRECTION FOR DRIVE, TILT, AND SCANNING-SPEED ERRORS IN IMAGING SYSTEMS

(71) Applicant: NeuroLogica Corporation, Danvers, MA (US)

(72) Inventors: Philip Sullivan, Danvers, MA (US); Matthew Christensen, Danvers, MA (US); Ibrahim Bechwati, Waltham, MA (US); Ross Caisse, Danvers, MA (US)

(73) Assignee: NeuroLogica Corporation, a subsidiary of Samsung Electronics Co., Ltd., Danvers, MA (US)

( * ) Notice: Subject to any disclaimer, the term of this patent is extended or adjusted under 35 U.S.C. 154(b) by 223 days.

(21) Appl. No.: 15/472,930

(22) Filed: Mar. 29, 2017

(65) Prior Publication Data

US 2017/0281117 A1    Oct. 5, 2017

Related U.S. Application Data

(60) Provisional application No. 62/314,441, filed on Mar. 29, 2016.

(51) Int. Cl.
| | |
|---|---|
| A61B 6/00 | (2006.01) |
| A61B 6/03 | (2006.01) |
| G06T 11/00 | (2006.01) |
| A61B 6/02 | (2006.01) |

(52) U.S. Cl.
CPC .............. *A61B 6/583* (2013.01); *A61B 6/027* (2013.01); *A61B 6/032* (2013.01); *A61B 6/44* (2013.01); *A61B 6/4405* (2013.01); *A61B 6/52* (2013.01); *A61B 6/5205* (2013.01); *A61B 6/54* (2013.01); *A61B 6/58* (2013.01); *A61B 6/582* (2013.01); *G06T 11/005* (2013.01); *A61B 6/547* (2013.01); *A61B 6/584* (2013.01); *G06T 2211/40* (2013.01)

(58) Field of Classification Search
CPC ....... A61B 6/027; A61B 6/032; A61B 6/4405; A61B 6/52; A61B 6/5205; A61B 6/582; A61B 6/583; A61B 6/584; A61B 6/44; A61B 6/54; A61B 6/547; A61B 6/58
USPC ............................................ 378/4, 207, 901
See application file for complete search history.

(56) References Cited

U.S. PATENT DOCUMENTS

| | | | |
|---|---|---|---|
| 6,178,220 B1 * | 1/2001 | Freundlich ............ | G06T 11/003 378/15 |
| 6,400,789 B1 * | 6/2002 | Dafni ..................... | A61B 6/032 378/15 |
| 6,408,044 B2 * | 6/2002 | Sembritzki .......... | G01N 23/046 378/15 |
| 6,568,851 B2 * | 5/2003 | Saito ..................... | A61B 6/032 378/19 |
| 6,597,803 B1 * | 7/2003 | Pan ........................ | A61B 6/032 378/15 |
| 6,813,374 B1 * | 11/2004 | Karimi ............... | G06K 9/00771 378/207 |
| 7,175,347 B2 | 2/2007 | Tybinkowski et al. | |
| 7,428,290 B2 * | 9/2008 | Nishide .................. | A61B 6/032 378/4 |
| 7,555,097 B2 * | 6/2009 | Yamazaki .............. | A61B 6/032 378/19 |

(Continued)

*Primary Examiner* — Allen C. Ho
(74) *Attorney, Agent, or Firm* — Pandiscio & Pandiscio

(57) ABSTRACT

Methods for the correction of drive, tilt, and scanning-speed errors in imaging systems such as CT machines.

19 Claims, 14 Drawing Sheets

(56) References Cited

U.S. PATENT DOCUMENTS

| | | | |
|---|---|---|---|
| 7,724,866 B2* | 5/2010 | Naidu | G01T 1/2985 |
| | | | 378/15 |
| 8,358,824 B2* | 1/2013 | Hagiwara | A61B 6/032 |
| | | | 378/4 |
| 8,503,750 B2* | 8/2013 | Benson | A61B 6/5258 |
| | | | 378/4 |
| 8,686,368 B2 | 4/2014 | Tybinkowshi et al. | |
| 8,888,364 B2 | 11/2014 | Bailey et al. | |
| 9,208,918 B2* | 12/2015 | Tybinkowski | G21K 1/02 |
| 9,852,526 B2* | 12/2017 | Nakanishi | G06T 11/005 |

* cited by examiner

CORRECTION FOR DRIVE, TILT, AND SCANNING-SPEED ERRORS IN IMAGING SYSTEMS

REFERENCE TO PENDING PRIOR PATENT APPLICATION

This patent application claims benefit of pending prior U.S. Provisional Patent Application Ser. No. 62/314,441, filed Mar. 29, 2016 by Samsung Electronics Co., Ltd. and Philip Sullivan et al. for CORRECTION FOR DRIVE AND TILT ERRORS IN MOBILE CT MACHINES, which patent application is hereby incorporated herein by reference.

FIELD OF THE INVENTION

This invention relates to imaging systems (sometimes also referred to as scanners) in general, and more particularly to mobile imaging systems (sometimes also referred to as mobile scanners).

BACKGROUND OF THE INVENTION

CT Imaging Systems in General

In many situations it can be desirable to image the interior of opaque objects. By way of example but not limitation, in the medical field, it can be desirable to image the interior of a patient's body so as to allow viewing of internal structures without physically penetrating the skin.

Computed Tomography (CT) has emerged as a key imaging modality in the medical field. CT imaging systems generally operate by directing X-rays into the body from a variety of positions, detecting the X-rays passing through the body, and then processing the detected X-rays so as to build a three-dimensional (3D) data set of the patient's anatomy. This 3D data set can then be processed so as to create a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown an exemplary CT imaging system 5. CT imaging system 5 generally comprises a torus 10 which is supported by a base 15. A center opening 20 is formed in torus 10. Center opening 20 receives the patient anatomy which is to be scanned.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions so as to enable CT imaging system 5 to create a "slice" image of the anatomy penetrated by the X-ray beam. Furthermore, by moving the patient and CT imaging system 5 relative to one another during scanning, a series of slice images can be acquired, and thereafter appropriately processed, so as to create a 3D data set of the scanned anatomy. This 3D data set can then be processed so as to create a 3D computer model of the scanned anatomy. In practice, it is common to configure X-ray detector assembly 30 so that multiple slice images (e.g., 8 slices, 16 slices, 32 slices, etc.) may be acquired with each rotation of rotating disc 23, whereby to speed up the acquisition of scan data.

And in practice, it is now common to effect helical scanning of the patient's anatomy so as to generate a 3D data set of the scanned anatomy, which can then be processed so as to create a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

The DICOM Standard

Thus, with a CT imaging system, a series of slice images of the patient's anatomy are acquired, these slice images can be aggregated together so as to form a 3D data set, and the 3D data set can be processed so as to create a 3D computer model.

In practice, the series of slice images are typically transmitted between systems (e.g., the CT imaging system and a hospital PACs system) in a streamed serial data transmission using the so-called DICOM standard which specifies, in a header for the streamed serial data transmission, the width and height parameters of each slice and the spacing parameter between the slices, thereby enabling the series of slice images to be reconstructed at the receiving end using the header information and the scan data in the streamed serial data transmission.

Mobile CT Imaging Systems

CT imaging systems for imaging a patient have traditionally consisted of a fixed-position CT machine and a movable scanning platform for supporting the patient and for moving the patient relative to the fixed-position CT machine during scanning (e.g., a movable scanning platform which moves into the center bore of a fixed-position CT machine, whereby to allow the fixed-position CT machine to scan the anatomy of a patient positioned on the movable scanning platform as the movable scanning platform moves through the center bore of the fixed-position CT machine). Such fixed-position CT machines are typically quite large and traditionally located inside a radiology suite within a medical facility.

However, locating a fixed-position CT machine in a radiology suite requires that the patient be moved to the radiology suite when the patient needs to be scanned, which can be inconvenient (e.g., with bedridden patients) and time-consuming (i.e., since the patient must be brought from their current location to the radiology suite). Among other things, this can be problematic in time-critical situations, e.g., where a stroke victim must be rapidly scanned in order to determine the nature of their stroke (i.e., ischemic or hemorrhagic) so that the patient can then receive the appropriate treatment (e.g., the administration of tPA or not).

In addition, in many cases it can be advantageous to scan a patient in an operating room before and/or during a surgical procedure.

By way of example but not limitation, prior to placing surgical implants into the body of a patient, it is often important to obtain a 3D map of the anatomical region in which the implant will be positioned. Typically, pre-surgical scanning is conducted, e.g., using a CT machine. The surgery is then planned out in advance using the pre-surgical scans. Typically the patient will be scanned in a radiology suite days (and sometimes weeks) prior to the surgery. The pre-surgical scans are then used during the surgery to navigate through the anatomical region in which the implant will be positioned. However, the human body is not a rigid object. As such, the anatomy may shift and the patient status may change in the time between the pre-surgical scanning and the surgical procedure, which may render the pre-surgical scans inaccurate and/or obsolete. Therefore, it can be highly advantageous to scan the patient again immediately before commencing the surgical procedure. Furthermore, the anatomy may shift again during the surgery itself, and hence it can be highly advantageous to scan the patient again during the surgical procedure itself.

By way of further example but not limitation, intraoperative scanning is a common procedure where scans are taken before, during and after a surgical procedure. More particularly, pre-surgical scans are taken to help locate an anatomical abnormality prior to the surgery. Intraoperative scans are taken during the surgery to confirm the success of removing abnormal anatomical objects (e.g., cancerous cells). The patient may then be taken to a recovery room and scanned again after a period of time (which can be up to 24 hours after the surgery) to determine if the surgery was successful. The patient may then be rescheduled for a second surgical procedure based on the outcome of the post-surgical scan.

For these and other reasons, mobile CT machines have been developed which allow the CT machine to be physically moved from one area of a medical facility to another area of the medical facility (e.g., from a radiological suite to an operating room) so that the patient can be scanned at their current location (e.g., on the surgical table). With such mobile CT machines, the CT machine is also configured to move relative to the patient during scanning, so that the patient can be scanned on any support platform (e.g., a standard operating room table) without having to be moved onto a special movable scanning platform (e.g., such as the special movable scanning platforms typically used in radiological suites with fixed-position CT machines). Thus, with such mobile CT machines, a patient can be scanned in real-time in the operating room, allowing the surgeon to have a clear map of the anatomy of the patient without having to rely on outdated scans.

In order for the mobile CT machines to initially move to the patient, and to thereafter move relative to the patient during scanning, the CT machine is provided with (i) a "gross movement mechanism" for moving the CT machine over relatively large distances (e.g., from one room to another), and (ii) a "fine movement mechanism" for moving the CT machine during scanning.

In one preferred form of mobile CT machine, and looking now at FIGS. 4 and 5, base 15 of CT imaging system 5 may comprise a transport assembly 50 for (i) moving mobile CT imaging system 5 to the location of the patient prior to scanning, and (ii) moving the CT imaging system relative to the patient during scanning. More particularly, transport assembly 50 may comprise (i) a gross movement mechanism 55 for moving CT imaging system 5 relatively quickly across room distances, so that the CT imaging system can be quickly and easily brought to the patient, such that the patient can be scanned at their current location without needing to be moved to a radiology suite, and (ii) a fine movement mechanism 60 for moving the CT imaging system precisely, relative to the patient, during scanning so that the patient can be scanned on a standard operating room table or bed or gurney without needing to be moved onto a special movable scanning platform (e.g., such as the special movable scanning platforms typically used in radiological suites with fixed-position CT machines).

In one preferred form of the invention, gross movement mechanism 55 may comprise a plurality of free-rolling casters 62, and fine movement mechanism 60 may comprise a plurality of centipede belt drives ("centipedes") 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging system 5.

Thus, with a mobile CT imaging system 5, the mobile CT imaging system may be pre-positioned in an "out of the way" location (e.g., in an unused corner of an operating room or recovery room) and then, when a patient requires scanning, the patient may be quickly and easily scanned at their current location, by simply moving the mobile CT imaging system to the patient's bedside on gross movement mechanism 55 (e.g., on casters 62), and thereafter moving the mobile CT imaging system during scanning on fine movement mechanism 60 (e.g., on centipede belt drives 63).

In the foregoing discussion, the "gross movement mechanism" is described in the context of lowerable free-rolling casters which can be selectively engaged with the floor so that the CT machine can be rolled from one area of a medical facility to another area of the medical facility, and the "fine movement mechanism" is described in the context of centipede belt drives (centipedes) which can be selectively engaged with the floor and used to move the CT machine relative to the patient during scanning.

However, it should be appreciated that, for the purposes of the present invention, the aforementioned "gross movement mechanism", and the aforementioned "fine movement mechanism", may take other forms. By way of example but not limitation, the "gross movement mechanism" may comprise lowerable powered wheels which can be selectively engaged with the floor and used to drive the CT machine from one area of a medical facility to another area of the medical facility, and the "fine movement mechanism" may comprise other powered wheels which can be selectively engaged with the floor and used to move the CT machine relative to the patient during scanning.

Or, if desired, the "gross movement mechanism" and the "fine movement mechanism" may be embodied in a single set of powered wheels which can be selectively engaged with the floor and used to drive the CT machine from one area of a medical facility to another area of the medical facility, and to move the CT machine relative to the patient during scanning.

The present invention is intended to apply to all of the foregoing mobile CT machines, regardless of whether the "gross movement mechanism" comprises lowerable free-rolling casters, lowerable powered wheels, etc.; and/or the "fine movement mechanism" comprises a centipede belt drive, powered wheels, etc.; and/or the "gross movement mechanism" and the "fine movement mechanism" are embodied in a single set of drive wheels, etc. However, for the purpose of the following discussion, the "fine movement mechanism" may sometimes hereinafter be discussed in the context of centipede belt drives (i.e., centipedes). This is intended to be by way of example and not limitation.

For the purposes of the following discussion, it can also be helpful to identify the various axes associated with the mobile CT machine—to this end, the "X-axis" will be considered to be the horizontal axis extending parallel to the floor (i.e., the width of each scan slice), the "Y-axis" will be considered to be the vertical axis extending perpendicular to the floor (i.e., the height of each scan slice), and the "Z-axis" will be considered to be the axis extending through the scanning bore of the mobile CT machine (i.e., the thickness of each scan slice and the spacing between each scan slice). See FIG. 1.

Drive and Tilt Errors in Mobile CT Machines

Unfortunately, it has been found that errors can sometimes occur in the 3D data set generated by mobile CT machines. These errors are generally caused by irregularities in the floor over which the mobile CT machine must move during scanning, although they can also be caused by variations in the performance of select components of the mobile CT machine.

More particularly, it has been found that three types of errors can be introduced with respect to the Z-axis of the 3D data set. These errors relate to:

(i) inaccuracies in the movement of the mobile CT machine along the Z-axis during scanning, which can cause the scanner to acquire its scan slices at scan intervals other than the intended scan intervals and/or which can cause the scanner to be falsely positioned at non-uniform intervals as it acquires its scan slices, and hence cause the scanner to acquire its scan slices at non-uniform intervals (typically caused by irregularities in the floor over which the mobile CT machine moves during scanning, but sometimes also caused by variations in the performance of the "fine movement mechanism" during scanning)—these types of errors are sometimes hereinafter referred to as "drive errors" ($\Delta I$)(see FIG. 6);

(ii) changes in the tilt of the mobile CT machine as the mobile CT machine moves relative to the patient during scanning (typically caused by irregularities in the floor over which the mobile CT machine moves during scanning)—these types of errors are sometimes hereinafter referred to as "tilt errors" ($\Delta \beta$) (see FIG. 6); and (iii) changes in the scanner speed as it translates over the patient during continuous scanning (typically caused by irregularities in the floor over which the mobile CT machine moves during scanning, but sometimes also caused by variations in the performance of the "fine movement mechanism" which moves the scanner during scanning).

A. Inaccuracies in the Movement of the Mobile CT Machine Along the Z-Axis During Scanning When the "fine movement mechanism" of the mobile CT machine is to move the mobile CT machine along the Z-axis during scanning of the patient, the mobile CT machine's control system typically sends the appropriate number of stepper pulses to a stepper motor in the "fine movement mechanism" of the mobile CT machine so as to drive the mobile CT machine the desired distance along the floor. By way of example but not limitation, the mobile CT machine's control system might send 100 stepper pulses to the stepper motor in the "fine movement mechanism" of the mobile CT machine so as to move the mobile CT machine 10 mm along the floor, whereby to acquire 8 slices of image data, with the slice images being set 1.25 mm apart along the Z-axis (i.e., 8×1.25 mm=10 mm). As a result, when the scan data from the slice images are represented in the DICOM format, the header information for the streamed serial data transmission indicates that the slices are set 1.25 mm apart (and also specifies the width and height parameters of each slice), whereby to allow proper reconstruction of the 3D data set from the streamed serial data transmission.

However, in many cases, the mobile CT machine may actually move a slightly different distance (e.g., 9.93 mm) along the floor, e.g., due to variations in the floor over which the mobile CT machine moves, and possibly also due to variations in the performance of the "fine movement mechanism" during scanning. In this case, the 8 slices of image data are actually acquired over a distance of 9.93 mm, so that the slices should be set 1.24125 mm apart during image reconstruction in order to properly recreate the 9.93 mm of scanned structure. However, the drive error (9.93 mm of actual travel vs. 10.0 mm of anticipated travel) is not reflected in the header information for the DICOM data transmission, where the 8 slices are declared to be set 1.25 mm apart (since they are assumed to have been acquired over 10 mm of travel). As a result, when the DICOM data stream is received at the receiving end and the 3D data set is reconstructed from the streamed serial data transmission, the 8 slices actually acquired over a distance of 9.93 mm are reconstructed as having been acquired over a distance of 10 mm. While this "drive error" only results in a difference of 0.07% for the cited example, over the aggregate of thirty 10 mm scans, the accumulated error results in an error of 2.1 mm, which can cause substantial scan degradation. See FIG. 7.

It should also be noted that, in the above example, where the acquisition of the 8 slices is to be taken over a distance of 10 mm, and the spacing of the 8 slices is to be set at 1.25 mm per slice, the acquisition distance and slice spacing are actually fixed by the geometry of the X-ray detector assembly of the mobile CT machine, which is why the mobile CT machine and the DICOM transmission operate on the "assumption" that the 8 slices are acquired over 10 mm and that there is a spacing of 1.25 mm between slices. The error in the movement of the mobile CT machine along the Z-axis (i.e., the drive error), and correspondingly the error in the 3D data set, is therefore spread out among the 8 slices, for each DICOM transmission packet.

Another way of describing the problem is as follows. The 3D volume of the reconstructed scan structure is basically generated by stacking the scanned images generated by the individual scans (e.g., an individual scan consisting of an 8 slice packet, or an individual scan consisting of a 16 slice packet, or an individual scan consisting of a 32 slice packet, etc.) which were presumably acquired at uniform intervals in space. FIG. 7A shows the reconstruction errors or deficiency which can be caused by drive error (i.e., cause the scanner to be falsely positioned at non-uniform intervals as it acquires its scan slices. The top images in FIG. 7A show the actual scans based on the position of the scanner on the floor (the top left image shows the scanner moving as intended, the top center image shows the scanner moving less than intended, and the top right image shows the scanner moving further than intended). The bottom images in FIG. 7A show the reconstructed 3D volume as generated from the scanned sections from the top images in FIG. 7A (the bottom left image shows the 3D volume reconstructed from the scans obtained by the scanner when the scanner was moving as intended, the bottom center image shows the 3D volume reconstructed from the scans obtained by the scanner when the scanner was moving less than intended, and the bottom right image shows the 3D volume reconstructed from the scans obtained by the scanner when the scanner was moving further than intended). Each scan covers the same length "L", for example, let "L" be 10 mm.

In the top left and bottom left images, which represent the "ideal" scan scenario where the scanner was moving as intended, the scans cover an area of 40 mm as shown in the top left image, and the reconstructed 3D volume matches the scanned portion of the object as shown in the bottom left image and as such there is no error. Thus, in the "ideal" case, the scanner movements match the section width.

The top center image shows that during the third scan, the scanner is mis-positioned and the scanner travels a distance of 8 mm instead of 10 mm, causing the scanner to fall 2 mm short of its target (i.e., intended) movement. Thus, during the third scan, the scanner images a total volume of 38 mm. However, as seen in the bottom center image, the reconstructed 3D volume is 40 mm long since it was generated by stacking 4 scan sections each of 10 mm width. In this case, the 3D reconstructed volume and the actual scanned volume no longer match—the reconstructed volume will include duplicate slices, and the reconstructed 3D volume stretches the actual volume by 2 mm. As such, the distances in the 3D reconstructed volume will be larger than their counterparts in the true volume.

The top right and bottom right images show the error which occurs if the scanner "over-shoots" its target position (i.e., if the scanner moves further than intended). In this case, the reconstructed 3D volume will have missing slices. More particularly, the top right image shows that the "over-shooting" scanner images a volume over a distance of 42 mm. Again, the 3D reconstructed volume is always 40 mm long. In this case, the 3D reconstructed object (bottom right image) compresses the actual volume by 2 mm.

B. Changes in the Tilt of the Mobile CT Machine as the Mobile CT Machine Moves Relative to the Patient During Scanning It has also been discovered that changes in the tilt of the mobile CT machine can occur during scanning, and these changes in the tilt of the mobile CT machine can also affect the spacing between the acquired scan slices. More particularly, it has been found that irregularities in the floor upon which the mobile CT machine moves during scanning (e.g., inclines, declines, bumps, recesses, etc.) can cause the mobile CT machine to "tilt" as it moves through its scan stroke. As the tilt angle (see the tilt angle β in FIG. 6) varies, the orientation and the spacing of the slice images acquired by the mobile CT machine also varies. See FIG. 8. Significantly, as the height of the mobile CT machine (i.e., $d_{isocenter}$ in FIG. 8, which is the longitudinal axis of center opening 20 of CT imaging system 5) increases, and as the tilt of the mobile CT machine (i.e., the tilt angle β in FIG. 6) increases, the actual spacing of the scanned slices at the isocenter of the mobile CT machine (i.e., the longitudinal axis of center opening 20 of CT imaging system 5) also increases from the "theoretical spacing" (i.e., the spacing defined by the geometry of the X-ray detector assembly of the mobile CT machine). This difference between the actual spacing of the scanned slices and the expected spacing of the scanned slices is the "tilt error" referred to above.

By way of example but not limitation, the deviation in the slice spacing from its theoretical value (e.g., 1.25 mm where the 8 slices are collected over a 10 mm scan) vis-à-vis the actual value (e.g., 1.25875 mm where the upper portions of the 8 slices are collected over 10.07 mm due to machine tilt) can result in substantial scan degradation.

C. Compounding of Errors Due to Inaccuracies in Movement Along the Z-Axis and Tilt It will also be appreciated that the errors due to inaccuracies in the movement of the mobile CT machine along the Z-axis (i.e., drive error), and the errors due to machine tilt (i.e., tilt error), can compound, resulting in a sum of the two errors. See FIG. 9.

D. Changes in the Scanner Speed as it Translates Over the Patient During Continuous Scanning In continuous scanning, unlike the step-by-step scanning mode, the scan error may not be caused by an inaccuracy in the scan locations. More particularly, the scan error in the continuous scan mode may be caused by variations in the scanner translation speed, e.g., as the scanner moves over much larger distances on the scan floor. In the continuous scan mode, the scan distances can range anywhere from as low as 40 mm to as high as 1000 mm. In this case, the scan accuracy is dependent upon the speed of the scanner remaining uniform—however, the speed of the scanner may vary based on variations in the scan floor (i.e., the speed of the scanner may slow down if the scanner is climbing an incline, or the speed of the scanner may speed up if the scanner is descending a decline, etc.).

Unlike the step-by-step scanning mode, in the continuous scanning mode, an instantaneous correction cannot be applied to the scan spacing. As such, the scan correction must be accomplished in a different manner (see below).

SUMMARY OF THE INVENTION

It has now been discovered that it is possible to correct for errors due to inaccuracies in the movement of the mobile CT machine along the Z-axis (i.e., drive errors), and/or to correct for errors due to machine tilt (i.e., tilt errors), and/or to correct for changes in the speed of the mobile CT machine during continuous scanning, whereby to yield superior scan results.

In one preferred form of the invention, there is provided a method for characterizing the reconstruction parameters for scan data obtained by scanning an object with an imaging system, wherein the imaging system is intended to obtain X scan slices across a scan distance Y for reconstruction with a scan spacing of Y/X between adjacent scan slices, the method comprising:

scanning an object so as to obtain X scan slices;

identifying the actual scan distance Z across which the X scan slices were actually obtained;

calculating an actual scan spacing of Z/X which should be applied to the X scan slices so as to obtain an accurate reconstruction of the scan data; and characterizing the reconstruction parameters for the scan data as (i) the X scan slices, and (ii) the actual scan spacing of Z/X between adjacent scan slices.

In another preferred form of the invention, there is provided a method for creating a 3D reconstruction of a scanned object, the method comprising:

scanning a first region of an object so as to obtain X scan slices, and scanning an adjacent second region of an object so as to obtain X' scan slices;

identifying the actual scan distance Z across which the X scan slices were actually obtained, and identifying the actual scan distance Z' across which the X' scan slices were actually obtained;

calculating an actual scan spacing of (Z+Z')/(X+X') which should be applied to the X and X' scan slices so as to obtain an accurate reconstruction of the scan data; and creating a 3D reconstruction of the object by appending the X' scan slices having a scan spacing of (Z+Z')/(X+X') to the X scan slices having a scan spacing of (Z+Z')/(X+X').

In another preferred form of the invention, there is provided a method for characterizing the reconstruction parameters for scan data obtained by scanning an object with an imaging system, wherein the imaging system is intended to obtain X scan slices across a scan distance Y for reconstruction with a scan spacing of Y/X between adjacent scan slices, the method comprising:

scanning an object so as to obtain X scan slices;

identifying the angle of tilt B at which each of the X scan slices was obtained;

calculating ΔB for each of the X scan slices, where ΔB is the difference between the angle of tilt B for that scan slice and a vertical line;

finding the isocenter of the imaging system $d_{isocenter}$;

calculating tan (AB)×$d_{isocenter}$ for each of the X scan slices, and aggregating the results into a tilt correction factor C;

adding the tilt correction factor C to the scan distance Y so as to determine the actual scan distance Z across which the X scan slices were actually obtained;

calculating an actual scan spacing of Z/X which should be applied to the X scan slices so as to obtain an accurate reconstruction of the scan data; and characterizing the reconstruction parameters for the scan data as (i) the X scan slices, and (ii) the actual scan spacing of Z/X between adjacent scan slices.

In another preferred form of the invention, there is provided a method for creating a 3D reconstruction of a scanned object, the method comprising:

scanning a first region of an object so as to obtain X scan slices, and scanning an adjacent second region of an object so as to obtain X' scan slices;

identifying the angle of tilt B at which each of the X scan slices was obtained, and identifying the angle of tilt B' at which each of the X' scan slices was obtained;

calculating ΔB for each of the X scan slices, where ΔB is the difference between the angle of tilt B for that scan slice and a vertical line, and calculating ΔB' for each of the X' scan slices, where ΔB' is the difference between the angle of tilt B' for that scan slice and a vertical line;

finding the isocenter of the imaging system $d_{isocenter}$;

calculating tan (ΔB)×$d_{isocenter}$ for each of the X scan slices, and aggregating the results into a tilt correction factor C, and calculating tan (ΔB')×$d_{isocenter}$ for each of the X' scan slices, and aggregating the results into a tilt correction factor C';

adding the tilt correction factor C to the scan distance Y so as to determine the actual scan distance Z across which the X scan slices were actually obtained, and adding the tilt correction factor C' to the scan distance Y' so as to determine the actual scan distance Z' across which the X' scan slices were actually obtained;

identifying the actual scan distance Z across which the X scan slices were actually obtained, and identifying the actual scan distance Z' across which the X' scan slices were actually obtained;

calculating an actual scan spacing of (Z+Z')/(X+X') which should be applied to the X and X' scan slices so as to obtain an accurate reconstruction of the scan data; and creating a 3D reconstruction of the object by appending the X' scan slices having a scan spacing of (Z+Z')/(X+X') to the X scan slices having a scan spacing of (Z+Z')/(X+X').

In another preferred form of the invention, there is provided a method for characterizing the reconstruction parameters for scan data obtained by scanning an object with an imaging system, wherein the imaging system is intended to obtain X scan slices across a scan distance Y for reconstruction with a scan spacing of Y/X between adjacent scan slices, the method comprising:

scanning a calibrated phantom so as to calibrate the speed of the imaging system relative to the object to be scanned;

scanning the object so as to obtain X scan slices;

identifying the actual scan distance Z across which the X scan slices were actually obtained by adjusting the scan distance Y using the calibrated speed of the imaging system;

calculating an actual scan spacing of Z/X which should be applied to the X scan slices so as to obtain an accurate reconstruction of the scan data; and characterizing the reconstruction parameters for the scan data as (i) the X scan slices, and (ii) the actual scan spacing of Z/X between adjacent scan slices.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENT

The present invention comprises the provision and use of a novel method for correcting errors in the 3D data set generated by a mobile CT machine due to inaccuracies in the movement of the mobile CT machine along the Z-axis (i.e., drive errors), and/or due to machine tilt (i.e., tilt errors), whereby to yield superior scan results.

More particularly, it has been found that it is possible to compute a "correction factor", to be applied to the "theoretical spacing" for the acquired scan images, in order to compensate for errors due to inaccuracies in the movement of the mobile CT machine along the Z-axis (i.e., drive errors) and/or to compensate for errors due to machine tilt (i.e., tilt errors), whereby to yield superior scan results.

Correction for Errors Due to Inaccuracies in the Movement of the Mobile CT Machine Along the Z-axis (i.e., Drive Errors)

Figure 10:
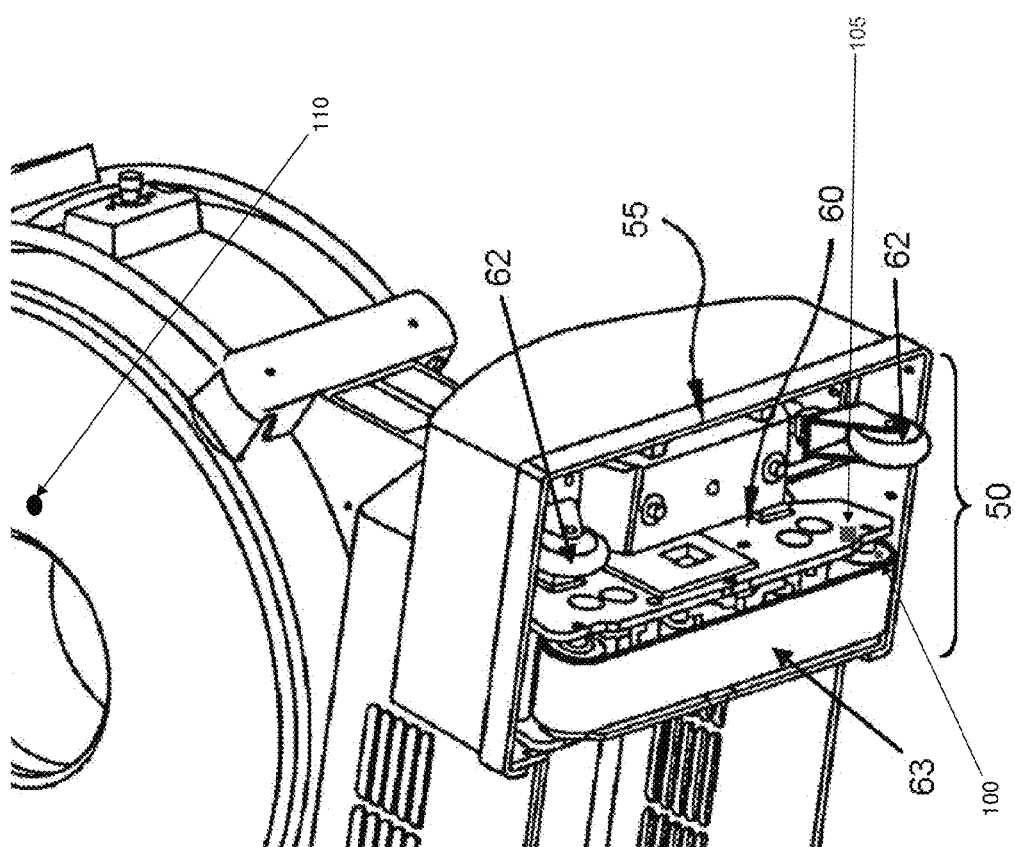
FIG. 10 is a schematic view showing how an encoder may be positioned on the fine movement mechanism of a mobile CT machine so as to more accurately detect movement of the mobile CT machine along the Z-axis, and how a tilt sensor may be positioned on the torus of the mobile CT machine so as to detect tilt of the mobile CT machine.

In one form of the invention, an encoder is provided on the fine movement mechanism that accurately measures the actual distance traveled by the mobile CT machine. By way of example but not limitation, and looking now at FIG. 10, the encoder may comprise a marker 100 which is mounted to a wheel of the fine movement mechanism and a reader 105 which is mounted to the chassis of the mobile CT machine, whereby to accurately record each revolution of the wheel of the fine movement mechanism and hence the actual distance traveled by the mobile CT machine. By comparing the actual distance traveled by the mobile CT machine (e.g., 9.93 mm) against the "theoretical travel" of the mobile CT machine (e.g., 10.0 mm), the actual $\Delta I$ (i.e., 10.0 mm−9.93 mm=0.07 mm), which is the error due to inaccuracies in the movement of the mobile CT machine along the Z-axis (i.e., the drive error), can be known. This $\Delta I$ can then be used to calculate the actual spacing between scan slices (i.e., 9.93 mm/8 slices=1.24125 mm/slice), and this information can be encoded in the header of the DICOM data transmission.

Note that other means may be used to determine the actual distance traveled by the mobile CT machine, e.g., optical sensors, radar (ultrasound) sensors, etc.

Another method of correction is to use the actual distances traveled by the mobile scanner (determined by using any of the methods described above) and re-generating a uniformly-spaced 3D volume using the equivalent slice width calculated earlier.

Correction for Errors Due to Machine Tilt (i.e., Tilt Errors)

And in one form of the invention, a high precision tilt sensor 110 (FIG. 10) is rigidly attached to the torus of the mobile CT machine, and over the course of an axial or helical scan, the tilt of the mobile CT machine is measured for each scan slice, whereby to measure $\Delta \beta$ at each scan slice, where $\Delta \beta$ for that scan slice is the difference between the actual tilt of the mobile CT machine at the time of that scan slice and the theoretical tilt of the mobile CT machine (where the theoretical tilt of the mobile CT machine is no tilt, i.e., the mobile CT machine is perfectly vertical). Then $\tan(\Delta \beta) \times d_{isocenter}$ is calculated for each scan slice so as to determine the distance error associated with that scan slice due to the tilting of the mobile CT machine at the isocenter of the center opening 20 of mobile CT imaging system 5 while that scan slice is being obtained. This distance error associated with each scan slice is the "tilt error" discussed above. The distance errors associated with the $\Delta \beta$ for each of the scan slices can then be aggregated into a single distance error across the set of scan slices, and this aggregated distance error can then be used to adjust the scan distance value encoded in the DICOM header.

By way of example but not limitation, suppose 8 scan slices are to be acquired across 10.0 mm. Supposed further that distance errors associated with the $\Delta \beta$ for each of the 8 scan slices aggregate to a total of 2.8 mm. Then the actual distance over which the 8 scan slices are acquired (i.e., 10.0 mm+2.8 mm=12.4 mm) will yield a scan spacing of 1.6 mm (i.e., 12.8 mm/8 slices=1.6 mm/slice). Note how this differs from the "theoretical spacing" of 1.25 mm where a non-tilting mobile CT machine acquires 8 scan slices over a true 10.0 mm scan stroke (i.e., 10.0 mm/8 slices=1.25 mm/slice).

Simultaneously Correcting for Both Drive Error and Tilt Error

In one preferred form of the invention, it is possible to simultaneously correct for both drive error and tilt error. This is done by combining the drive error and tilt error into a single resultant, and then applying this resultant to the "theoretical" slice separation before determining the actual slice separation.

Figure 1:
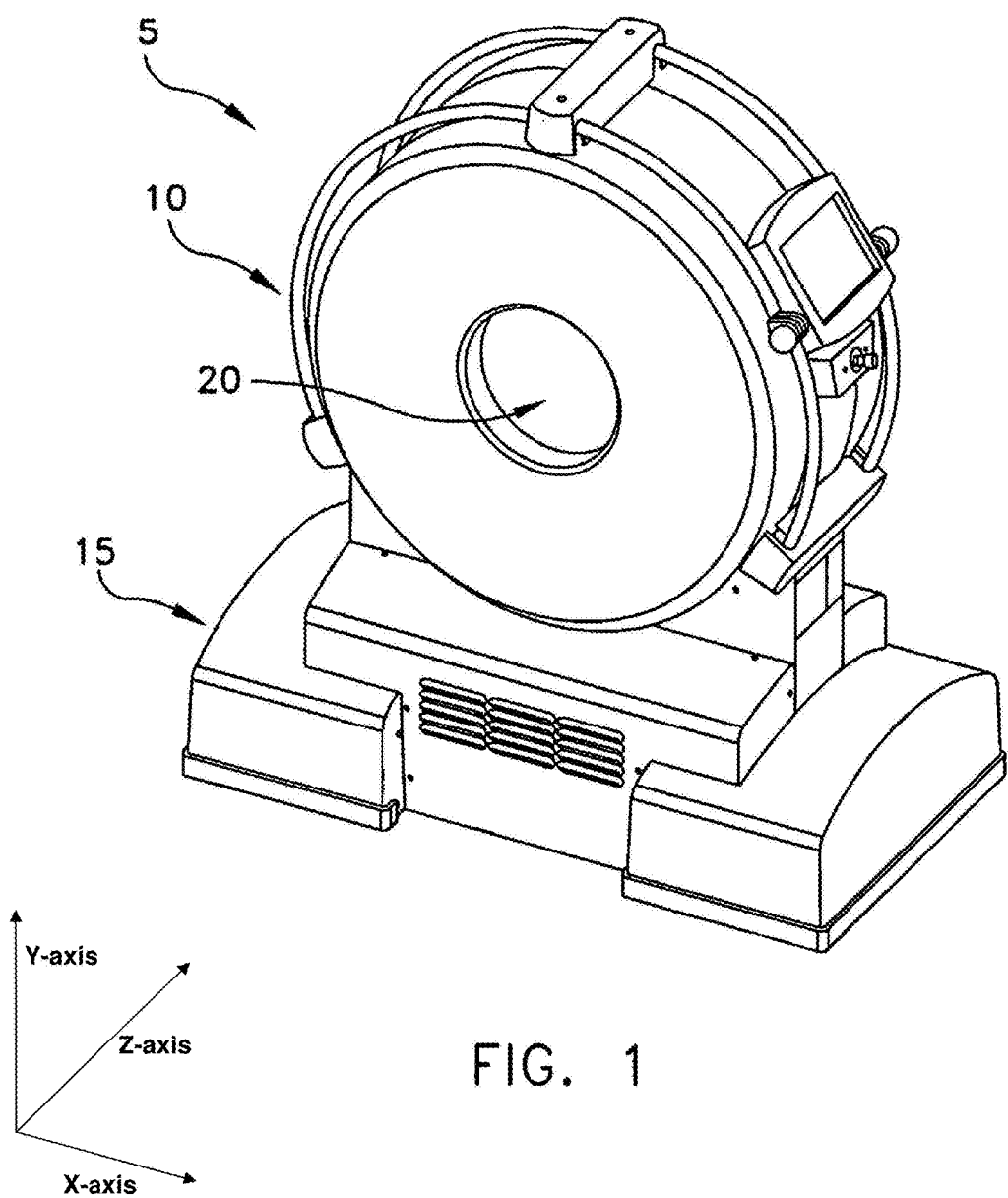
FIGS. 1 and 2 are schematic views showing the exterior of an exemplary CT imaging system.
Figure 2:
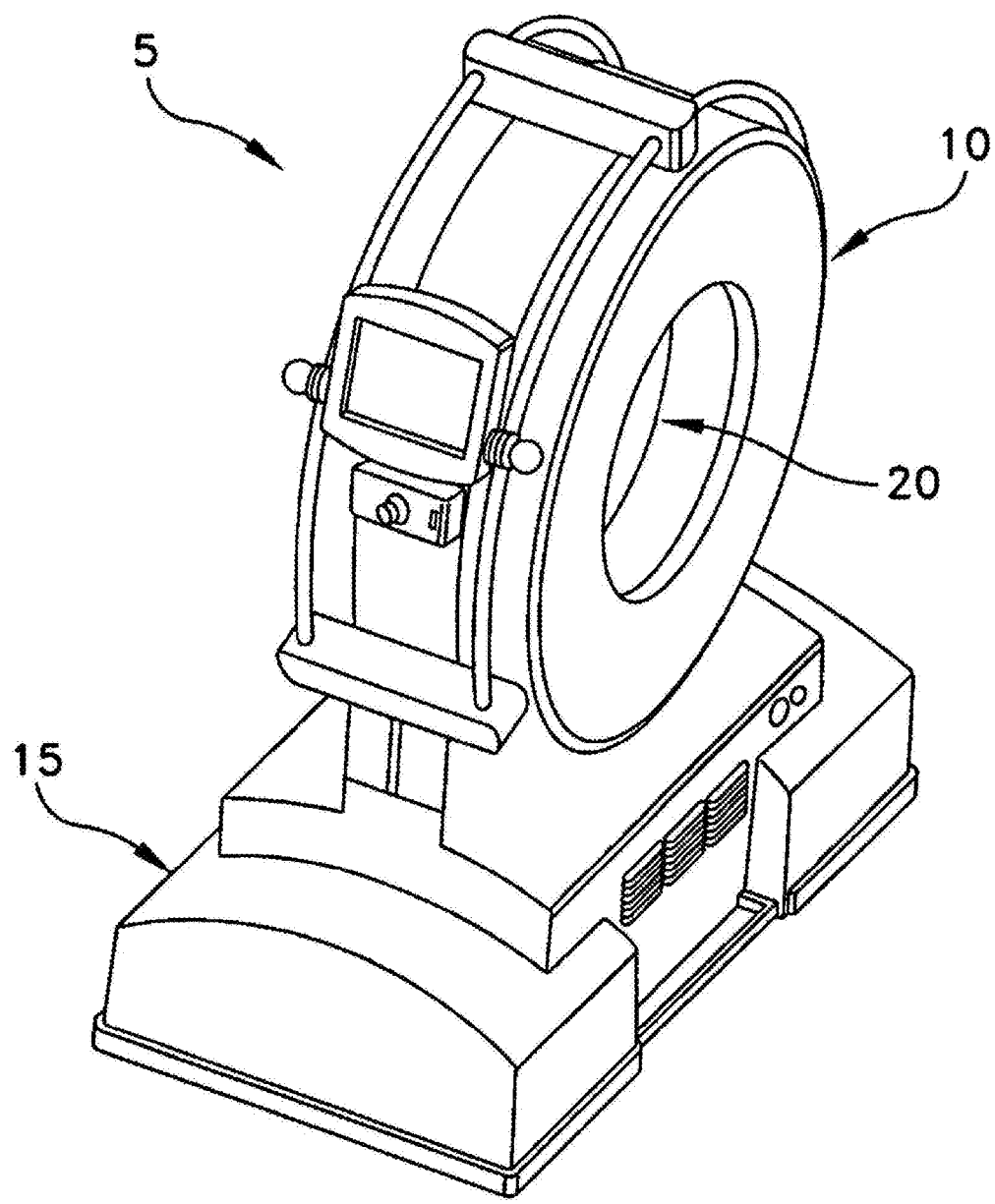
Figure 3:
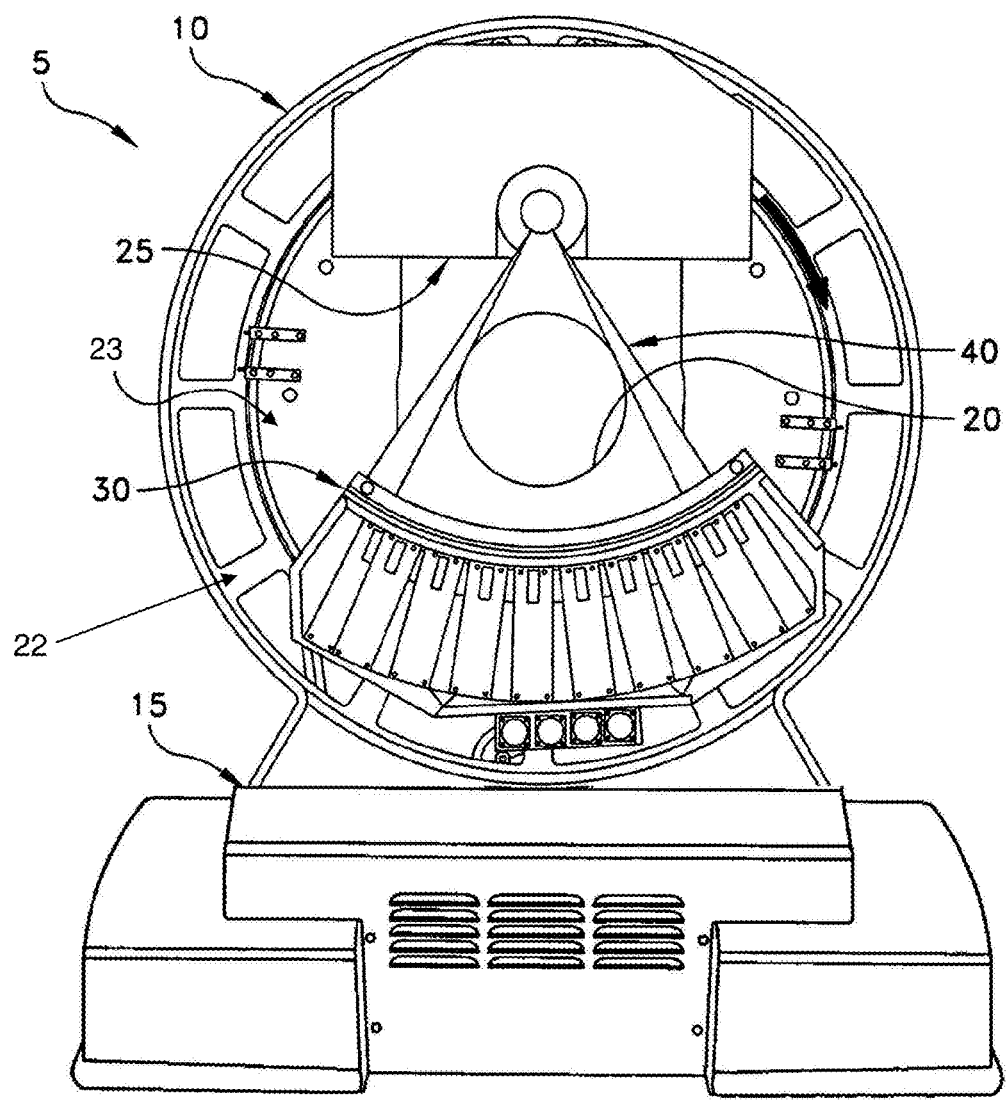
FIG. 3 is a schematic view showing various components in the torus of the exemplary CT imaging system shown in FIGS. 1 and 2.
Figure 4:
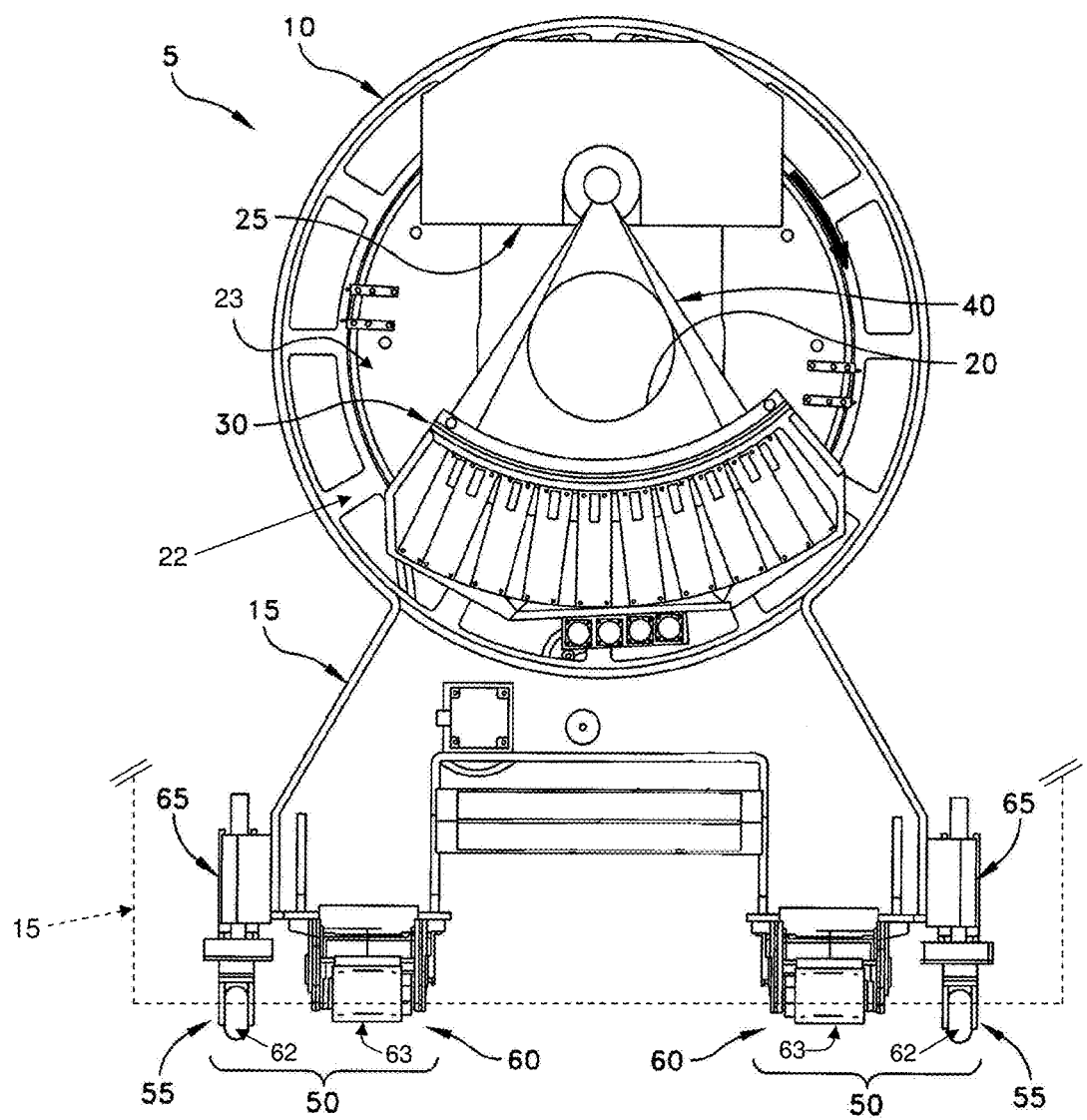
FIGS. 4 and 5 are schematic views showing an exemplary transport assembly for an exemplary mobile CT imaging system.
Figure 5:
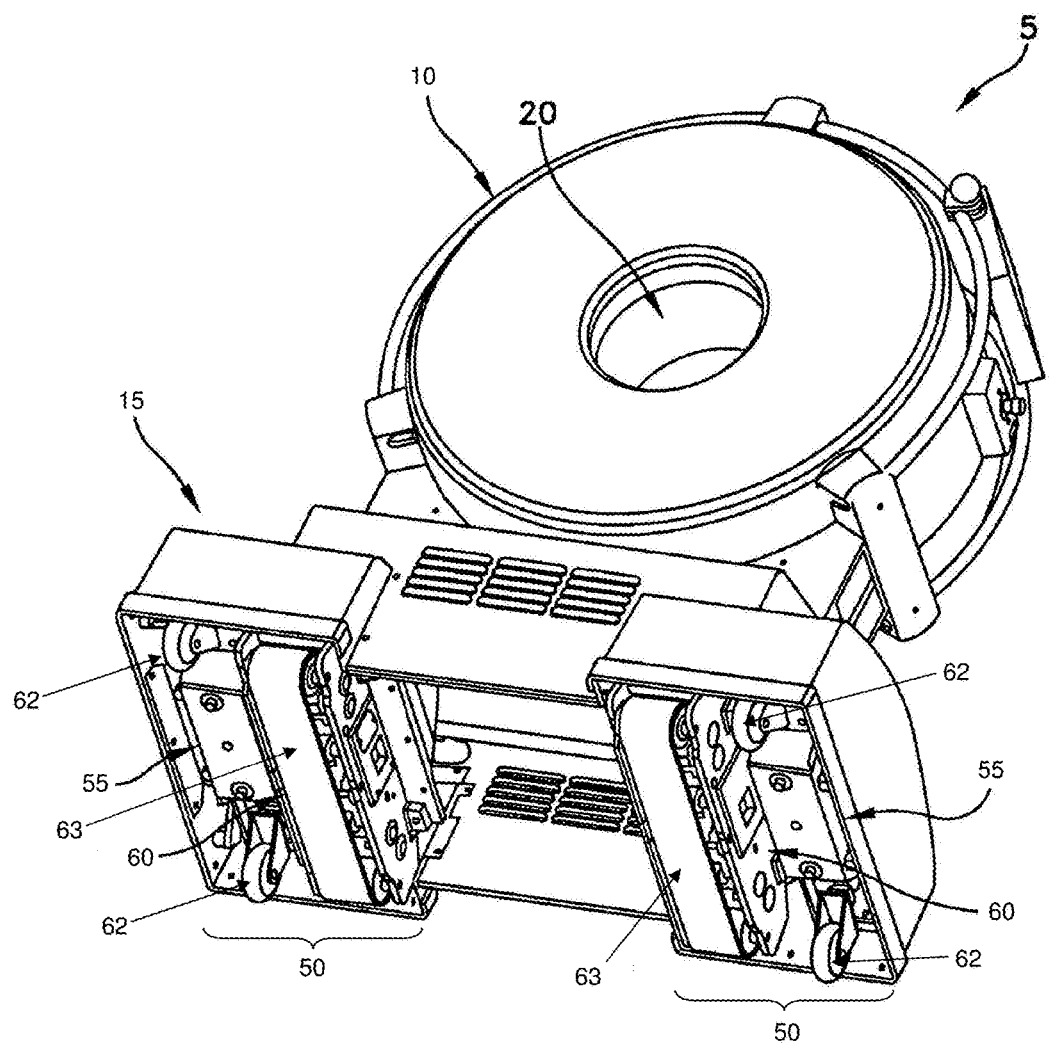
Figure 6:
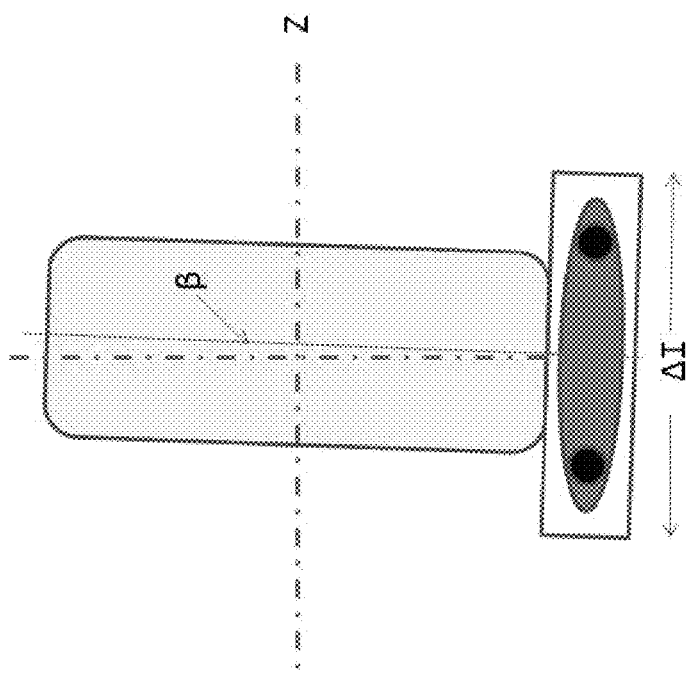
FIG. 6 is a schematic view showing two possible sources of error in the 3D data set generated by a mobile CT machine, namely, errors due to inaccuracies in the movement of the mobile CT machine along the Z-axis (i.e., drive errors), and errors due to machine tilt (i.e., tilt errors)
Figure 7:
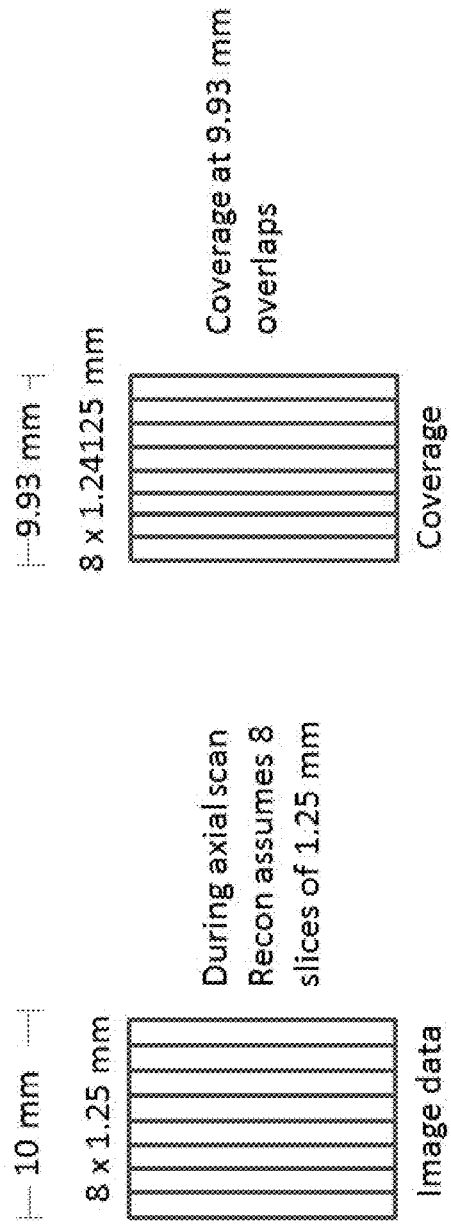
FIG. 7 is a schematic view showing further details of how errors may occur in the 3D data set generated by a mobile CT machine due to inaccuracies in the movement of the mobile CT machine along the Z-axis (i.e., drive errors)
Figure 7A:
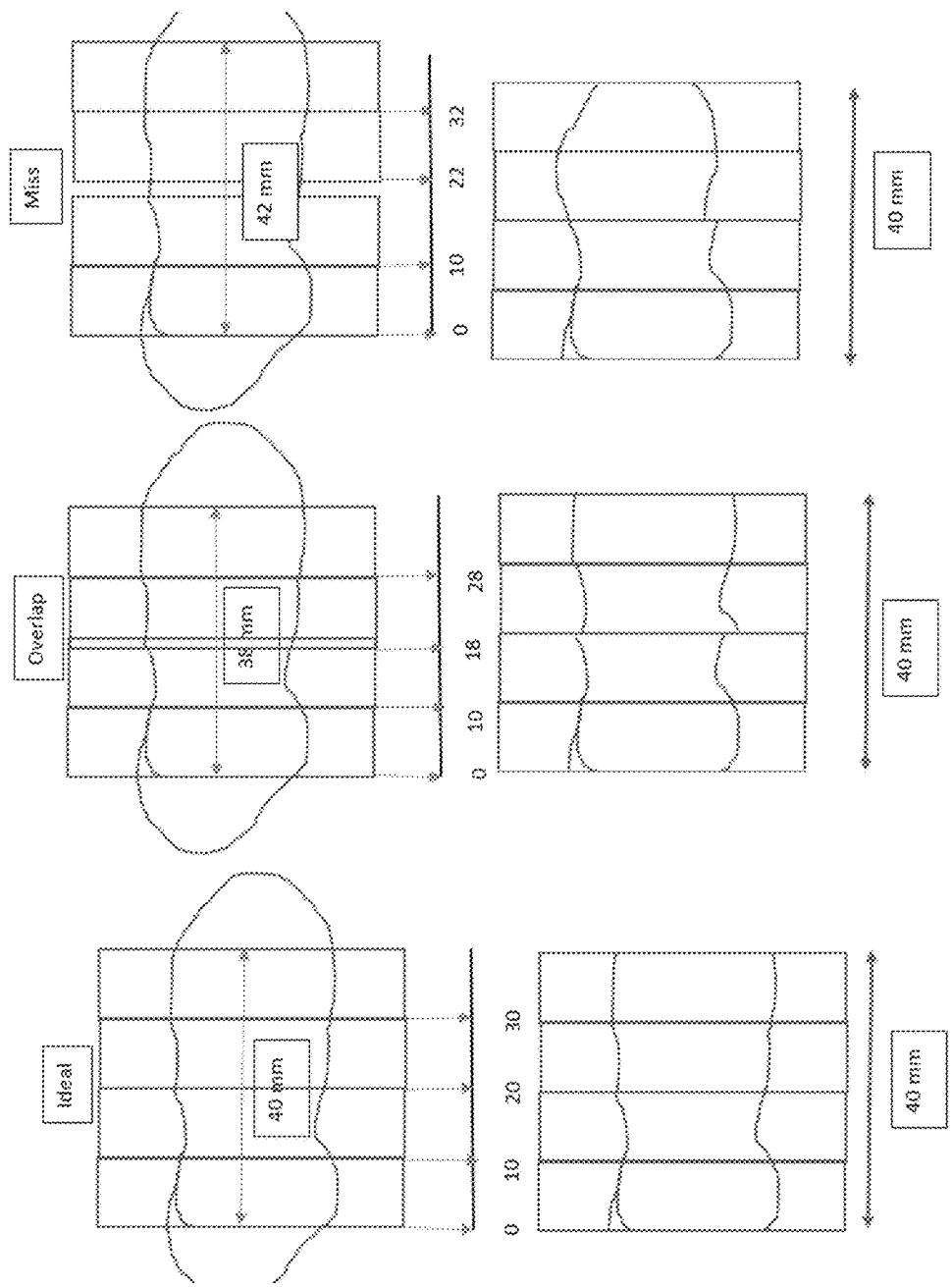
FIG. 7A is a schematic view showing how inaccuracies in the movement of the mobile CT machine can create errors in the 3D data set generated by the mobile CT machine, and these errors in the 3D data set generated by the mobile CT machine can in turn create errors in 3D volume reconstructed from the 3D data set.
Figure 8:
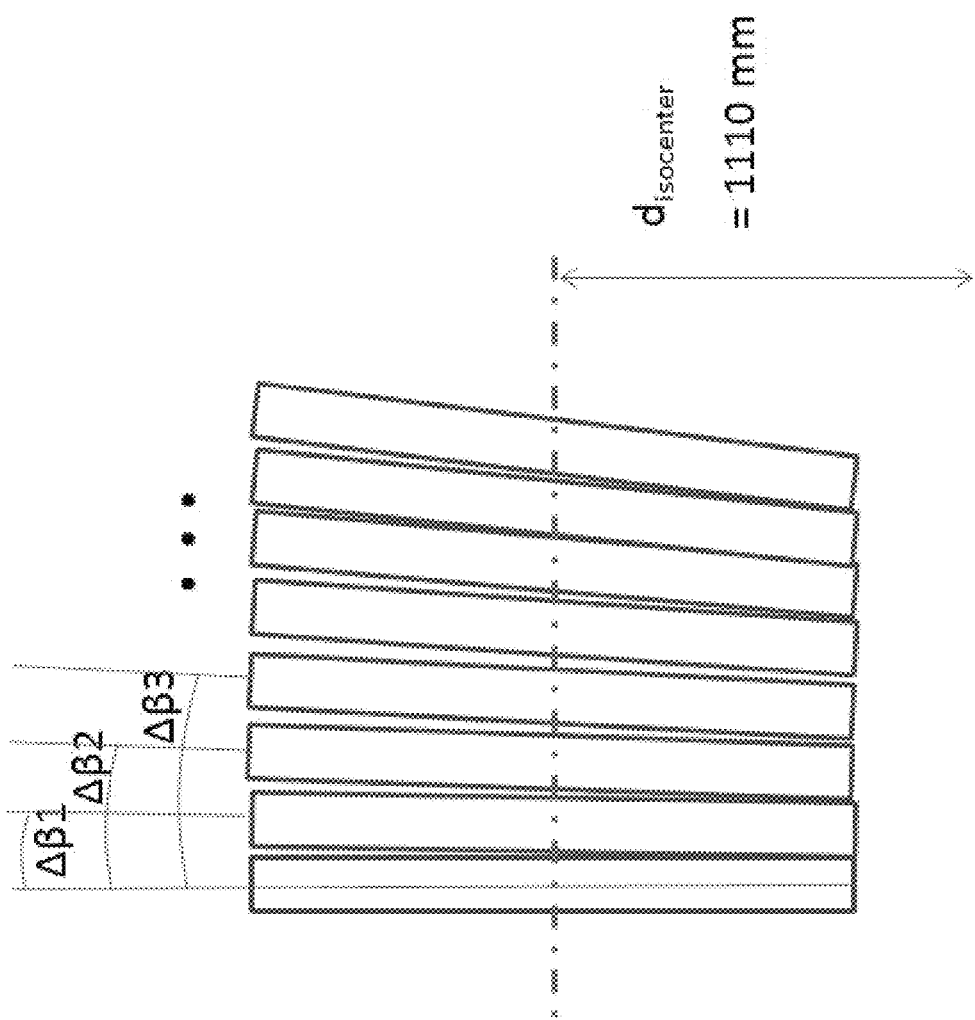
FIG. 8 is a schematic view showing further details of how errors may occur in the 3D data set generated by a mobile CT machine due to machine tilt (i.e., tilt errors)
Figure 9:
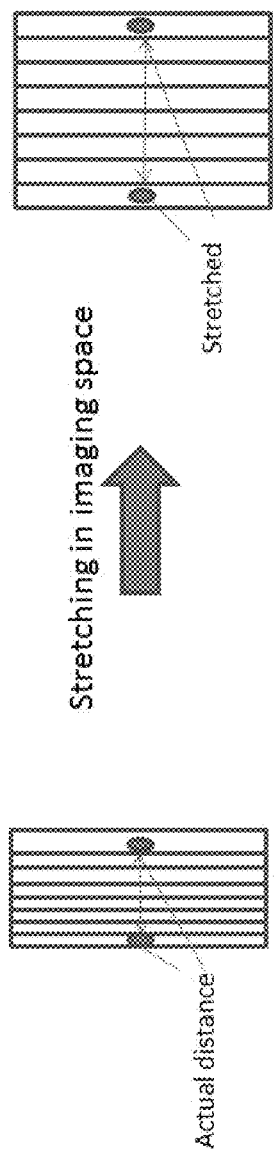
FIG. 9 is a schematic view showing how the errors due to inaccuracies in the movement of the mobile CT machine along the Z-axis (i.e., drive errors), and the errors due to machine tilt (i.e., tilt errors), can compound, resulting in a sum of the two errors.
Figure 9:

More particularly, in this form of the invention, the two aforementioned values $\Delta I$ and $\tan(\Delta \beta) \times d_{isocenter}$ are used to calculate a single correction factor (CF) to be applied to the "theoretical" slice separation distance (e.g., 1.25 mm in the example shown in FIG. 7, where 8 slices are expected to be acquired over a distance of 10 mm) so as to determine an "actual" slice separation distance (i.e., 1.25 mm+/−the difference introduced by the $\Delta I$ error and the $\tan(\Delta \beta) \times d_{isocenter}$ error). This actual slice separation distance is then encoded in the DICOM data transmission.

In one preferred form of the invention, this correction factor is a simple normalization: the value is the actual distance traveled (i.e., the expected/commanded distance traveled less the distance error associated with the drive error and less the distance error associated with the tilt error) is determined, and then this calculated actual distance traveled is divided by the expected/commanded distance which was to be traveled so as to provide a ratio, which is the correction factor—and then this ratio (i.e., the correction factor) is applied (i.e., multiplied against) the value of the expected slice separation to determine the actual slice separation. This actual slice separation is then the value which is encoded in the DICOM data transmission.

By way of example but not limitation, suppose the value of the actual distance traveled is 12.73 mm (i.e., suppose the expected/commanded distance traveled is 10.0 mm, suppose the distance error associated with the drive error is −0.07 mm and suppose the distance error associated with the tilt error is +2.8 mm, whereby to yield an actual distance traveled of 10.0 mm−0.07 mm+2.8 mm=12.73 mm). This calculated actual distance traveled (12.73 mm) is divided by the expected/commanded distance which was to be traveled (10.0 mm) so as to provide a ratio (12.73/10.0=1.273), which is the correction factor—and then this ratio (i.e., 1.273) is applied (i.e., multiplied against) the value of the expected slice separation (i.e., 1.25 mm) to determine the actual slice separation (i.e., 1.273×1.25 mm=1.59125 mm). This actual slice separation (i.e., 1.59125 mm) is then the value which is encoded in the DICOM data transmission.

"Look Up Table" (LUT)

In another preferred form of the invention, a pre-calculated "Look Up Table" (LUT) is used, where the LUT is based on previously-acquired floor data. More particularly, the mobile CT machine is run through a scan series. An encoder (e.g., such as the encoder 100, 105 of the sort described above) is used to determine drive error throughout the scan series. A tilt sensor (e.g., such as the tilt sensor 110 described above) reads the changes in tilt throughout a scan series. The final shape of the tilt data could be a "slant" of a certain magnitude, for example 0.1° over 600 mm, or perhaps a "hockey stick" configuration with a relative flat section over, for example 400 mm, with a sharp uptick over the last 200 mm. This actual tilt data can then be used to determine tilt error. The drive error and the tilt error can be matched to a pre-calculated correction factor which is used to correct the DICOM header information for the streamed serial data transmission.

Figure 11:
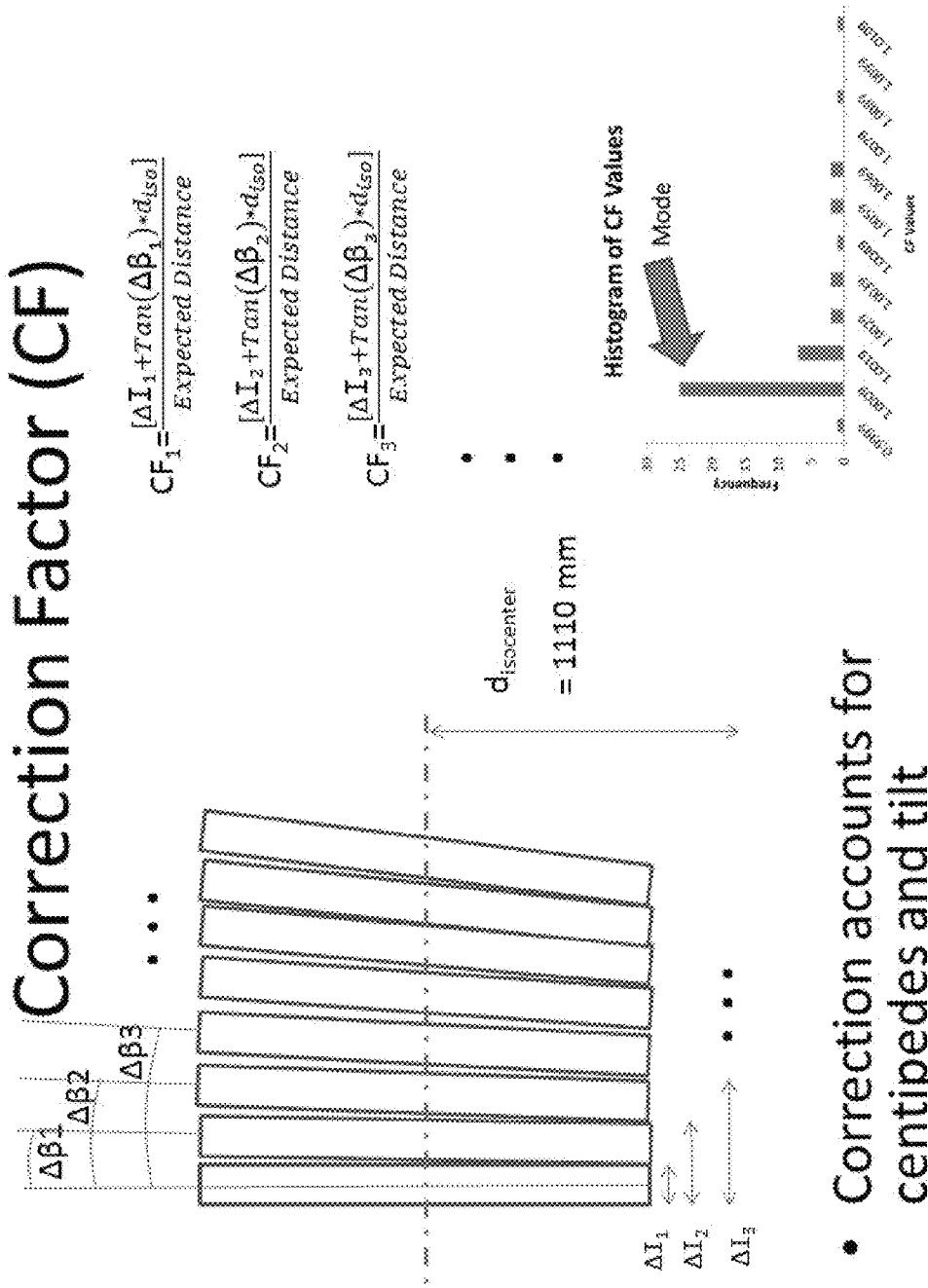
FIG. 11 is a schematic view showing how a correction factor can be calculated to correct for the errors due to inaccuracies in the movement of the mobile CT machine along the Z-axis (i.e., drive errors), and the errors due to machine tilt (i.e., tilt errors)
Figure 12:
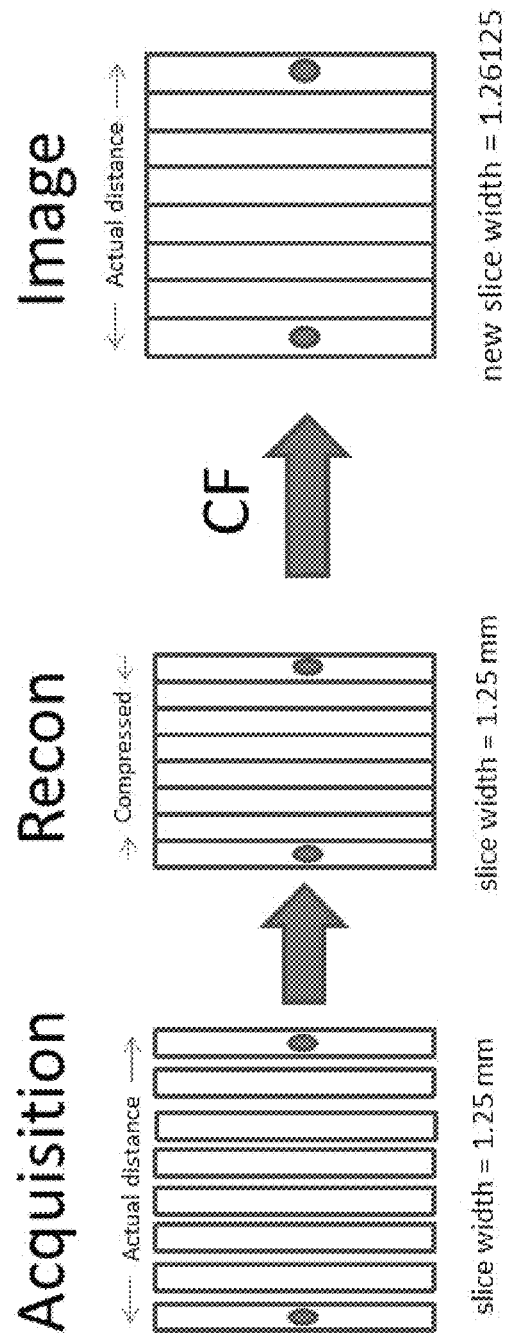
FIG. 12 is a schematic view showing how the aforementioned correction factor can be applied to correct for the errors due to inaccuracies in the movement of the mobile CT machine along the Z-axis, (i.e., drive errors) and the errors due to machine tilt (i.e., tilt errors).

By way of example but not limitation, suppose 8 slices of scan data are to be acquired over what is intended to be 10 mm of scan stroke on a floor which has variations (e.g., inclines, declines, bumps, recesses, etc.). The mobile CT machine is run through a series of test scans, where each test scan collects a series of actual distances traveled and a corresponding series of actual machine tilts. This test data is then used to calculate a correction factor (see FIGS. 11 and 12), e.g., 1.009, which is applied to the theoretical slice spacing of 1.25 mm to determine the actual slice spacing of 1.26125 mm. This actual slice spacing is then encoded in the DICOM data transmission so as to enable a more accurate slice reconstruction at the receiving end.

Correction for Errors Due to Changes in the Scanner Speed as it Translates Over the Patient During Continuous Scanning Scan errors due to changes in the scanner speed as it translates over the patient during continuous scanning are corrected using another process.

More particularly, in this form of the invention, using a special phantom with well-known distances, the speed of the scanner is calibrated based on the floor location. The calibration is accomplished as follow:

1. a calibrated bead phantom is positioned so that it can be scanned by the scanner—this calibrated bead phantom is used to provide the true, baseline (or "gold standard") distances used for measuring the scanner speed; in one preferred form of the invention, the phantom consists of a set of at least 13 beads that are spread over a distance greater than 500 mm, and the true distances are measured using a high precision computerized measuring machine (CMM) or any other high precision measurement device;

2. the bead phantom is scanned as the mobile CT machine moves over the scan floor in continuous motion;

3. an automated tool is used to measure the distances between the beads in the scanned volume—the beads distances in the scans are a function of the distance traveled by the mobile CT machine (the bead distances can also be measured using any image-viewing software equipped with measuring tools); and 4. the true bead distances measured using the high precision device are compared with the measured bead distances from the reconstructed 3D volume and the differences (or the ratio) between the two are used to adjust the nominal speed (i.e., the expected/commanded speed) of the scanner so as to determine the actual speed of the scanner.

By way of example but not limitation, if the largest measured bead distance is 502 mm (i.e., the measured bead distance obtained from the reconstructed scanned volume) while the corresponding true baseline distance (i.e., the "gold standard" distance) is 500 mm, this implies that the scanner is moving slower than expected (e.g., because the scanner is climbing an incline on the floor) and, as such, the nominal speed of the scanner should be increased by the ratio of the measured distance to the true distance in order to generate correct scan slice locations—in this example, the final speed of the scanner used to identify scan slice location during continuous scanning of the patient should be 502 mm/500 mm=1.004 of the scanner nominal speed.

Figure 13:
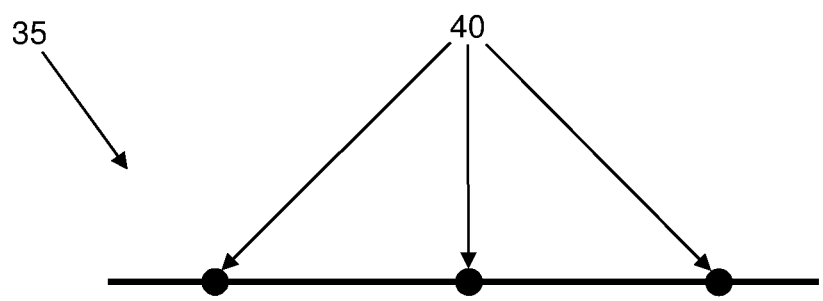
FIG. 13 is a schematic view showing a calibrated phantom formed in accordance with the present invention.

In other words, when using the scanner in continuous scanning mode so that the actual speed of the scanner influences the scan slice locations, the nominal speed of the scanner should be adjusted to the actual speed of the scanner in order to obtain the correct scan slice locations, and this can be done by (i) scanning a calibrated phantom (i.e., a calibrated phantom comprising a plurality of radioopaque objects, such as a calibrated phantom 35 comprising a plurality of beads 40 as shown in FIG. 13), (ii) comparing the locations of the calibrations in the reconstructed 3D volume with the actual locations of the calibrations in the calibrated phantom to determine the differences between the actual speed of the scanner and the nominal speed of the scanner, and (iii) then the nominal speed of the scanner can be adjusted so as to yield the correct scan slice locations during continuous scanning.

Application to Other Types of Mobile Scanning Machines that Generate a 3D Data Set by Moving the Mobile Scanning Machine Relative to the Patient During Scanning It should be appreciated that the present invention is also applicable to other types of mobile scanning machines that generate a 3D data set by moving the mobile scanning machine relative to the patient during scanning. By way of example but not limitation, the present invention may also be applied to a mobile SPECT machine such as is disclosed in U.S. Pat. No. 8,686,368.

It should also be appreciated that this invention could be applied to a mobile CT scanner that does not run along the floor itself, but instead runs along a rail system (which may be fixed to the floor or fixed to a carriage which is mobile relative to the floor). While a rail-mounted CT system might have less sharp $\Delta I$ and/or $\tan(\Delta\beta) \times d_{isocenter}$ deviations, the underlying tilt of the floor, plus any bending of the rails due to the weight of the CT system, may cause changes in tilt across a scan.

It should also be appreciated that this invention is not limited to mobile CT scanners, but also applies to fixed-position scanners with moving patient support platforms. In such applications, the patient support platform can also suffer from the same types of errors discussed above (e.g., drive errors, tilt errors, and scan speed errors), however, the errors can originate from the performance of the moving patient support platform. In addition, the errors can originate from movement of the patients during scanning.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for characterizing reconstruction parameters for scan data obtained by scanning an object with an imaging system, wherein the imaging system is intended to obtain X scan slices across a scan distance Y for reconstruction with a scan spacing of Y/X between adjacent scan slices, the method comprising:
    scanning an object so as to obtain X scan slices;
    identifying an actual scan distance Z across which the X scan slices were actually obtained;
    calculating an actual scan spacing of Z/X which should be applied to the X scan slices so as to obtain an accurate reconstruction of the scan data; and
    characterizing reconstruction parameters for the scan data as (i) the X scan slices, and (ii) the actual scan spacing of Z/X between adjacent scan slices.

2. A method according to claim 1, wherein the imaging system comprises a mobile CT machine.

3. A method according to claim 1, wherein the imaging system comprises a drive system comprising at least one rotary element, and further comprising identifying the actual scan distance Z by monitoring rotation of the at least one rotary element.

4. A method according to claim 3, wherein monitoring the rotation of the at least one rotary element comprises monitoring the rotation of the at least one rotary element with an encoder.

5. A method according to claim 1, wherein calculating the actual scan spacing of Z/X comprises calculating the actual scan spacing Z/X by (i) determining Z/Y, and (ii) determining Z/Y×Y/X.

6. A method for creating a 3D reconstruction of a scanned object, the method comprising:
    scanning a first region of an object so as to obtain X scan slices, and scanning an adjacent second region of the object so as to obtain X' scan slices;
    identifying an actual scan distance Z across which the X scan slices were actually obtained, and identifying an actual scan distance Z' across which the X' scan slices were actually obtained;
    calculating an actual scan spacing of (Z+Z')/(X+X') which should be applied to the X scan slices and the X' scan slices so as to obtain an accurate reconstruction of scan data; and
    creating a 3D reconstruction of the object by appending the X' scan slices having a scan spacing of (Z+Z')/(X+X') to the X scan slices having a scan spacing of (Z+Z')/(X+X').

7. A method for characterizing reconstruction parameters for scan data obtained by scanning an object with an imaging system, wherein the imaging system is intended to obtain X scan slices across a scan distance Y for reconstruction with a scan spacing of Y/X between adjacent scan slices, the method comprising:
    scanning an object so as to obtain X scan slices;
    identifying an angle of tilt B at which each of the X scan slices was obtained;
    calculating ΔB for each of the X scan slices, where ΔB is a difference between the angle of tilt B for each of the X scan slices and a vertical line;
    finding an isocenter of the imaging system $d_{isocenter}$;
    calculating tan (ΔB)×$d_{isocenter}$ for each of the X scan slices, and aggregating the calculated results into a tilt correction factor C;
    adding the tilt correction factor C to the scan distance Y so as to determine an actual scan distance Z across which the X scan slices were actually obtained;
    calculating an actual scan spacing of Z/X which should be applied to the X scan slices so as to obtain an accurate reconstruction of the scan data; and
    characterizing reconstruction parameters for the scan data as (i) the X scan slices, and (ii) the actual scan spacing of Z/X between adjacent scan slices.

8. A method according to claim 7, wherein the imaging system comprises a mobile CT machine.

9. A method according to claim 7, wherein the imaging system comprises a tilt sensor for identifying the angle of tilt B at which each of the X scan slices was obtained.

10. A method according to claim 7, wherein calculating the actual scan spacing of Z/X comprises calculating the actual scan spacing of Z/X by (i) determining Z/Y, and (ii) determining Z/Y×Y/X.

11. A method for creating a 3D reconstruction of a scanned object, the method comprising:
    scanning a first region of an object so as to obtain X scan slices, and scanning an adjacent second region of the object so as to obtain X' scan slices;
    identifying an angle of tilt B at which each of the X scan slices was obtained, and identifying an angle of tilt B' at which each of the X' scan slices was obtained;
    calculating ΔB for each of the X scan slices, where ΔB is a difference between the angle of tilt B for each of the X scan slices and a vertical line, and calculating ΔB' for each of the X' scan slices, where ΔB' is a difference between the angle of tilt B' for each of the X' scan slices and a vertical line;
    finding an isocenter of the imaging system $d_{isocenter}$;
    calculating tan (ΔB)×$d_{isocenter}$ for each of the X scan slices, and aggregating the calculated results into a tilt correction factor C, and calculating tan (ΔB')×$d_{isocenter}$ for each of the X' scan slices, and aggregating the calculated results into a tilt correction factor C';
    adding the tilt correction factor C to a scan distance Y so as to determine an actual scan distance Z across which the X scan slices were actually obtained, and adding the tilt correction factor C' to a scan distance Y' so as to determine an actual scan distance Z' across which the X' scan slices were actually obtained;
    identifying the actual scan distance Z across which the X scan slices were actually obtained, and identifying the actual scan distance Z' across which the X' scan slices were actually obtained;
    calculating an actual scan spacing of (Z+Z')/(X+X') which should be applied to the X scan slices and the X' scan slices so as to obtain an accurate reconstruction of scan data; and
    creating a 3D reconstruction of the object by appending the X' scan slices having a scan spacing of (Z+Z')/(X+X') to the X scan slices having a scan spacing of (Z+Z')/(X+X').

12. A method for characterizing reconstruction parameters for scan data obtained by scanning an object with an imaging system, wherein the imaging system is intended to obtain X scan slices across a scan distance Y for reconstruction with a scan spacing of Y/X between adjacent scan slices, the method comprising:
- scanning a calibrated phantom so as to calibrate a speed of the imaging system relative to the object to be scanned;
- scanning the object so as to obtain X scan slices;
- identifying an actual scan distance Z across which the X scan slices were actually obtained by adjusting a scan distance Y using the calibrated speed of the imaging system;
- calculating an actual scan spacing of Z/X which should be applied to the X scan slices so as to obtain an accurate reconstruction of scan data; and
- characterizing reconstruction parameters for the scan data as (i) the X scan slices, and (ii) the actual scan spacing of Z/X between adjacent scan slices.

13. A method according to claim 12, wherein the imaging system comprises a mobile CT machine.

14. A method according to claim 12, wherein the calibrated phantom comprises a phantom comprising a plurality of radioopaque objects disposed at known distances from one another.

15. A method according to claim 14, wherein the plurality of radiopaque objects comprise beads.

16. A method according to claim 12, further comprising calibrating the speed of the imaging system by creating a 3D reconstruction of the calibrated phantom and comparing the 3D reconstruction of the calibrated phantom to an actual calibrated phantom.

17. A method according to claim 16, further comprising obtaining the calibrated speed of the imaging system by modifying an intended speed of the imaging system according to a comparison of the 3D reconstruction of the calibrated phantom and the actual calibrated phantom.

18. A method according to claim 12, wherein calculating the actual scan spacing of Z/X comprises calculating the actual scan spacing of Z/X by (i) determining Z/Y, and (ii) determining Z/Y×Y/X.

19. A method according to claim 12, further comprising calculating an actual scan speed by (i) determining Z/Y, and (ii) determining Z/Y×an intended speed of the imaging system.

* * * * *